United States Patent [19]

Ignatjev

[11] 4,286,210
[45] Aug. 25, 1981

[54] AIR ION AND CHARGE DETECTOR

[76] Inventor: Vladimir Ignatjev, 39 Ledgewood Dr., Norwalk, Conn. 06850

[21] Appl. No.: 66,937

[22] Filed: Aug. 16, 1979

[51] Int. Cl.³ .............................................. G01N 31/02
[52] U.S. Cl. ...................... 324/72.5; 324/96; 324/457; 324/133; 340/784
[58] Field of Search .............. 350/331 R; 324/96, 72, 324/72.5, 158 P, 109, 452, 453, 457, 133; 340/784

[56] References Cited

U.S. PATENT DOCUMENTS

| | | |
|---|---|---|
| 2,187,541 | 1/1940 | Goranson et al. .................. 324/457 |
| 2,851,618 | 9/1958 | Korawinkel ........................ 324/109 |
| 3,337,801 | 8/1967 | Rinier et al. ...................... 324/72.5 |
| 3,627,408 | 12/1971 | Fergason ........................... 324/96 |
| 3,667,039 | 5/1972 | Garfein ............................. 324/96 |
| 3,915,555 | 10/1975 | Leibowitz .......................... 324/109 |

*Primary Examiner*—Michael J. Tokar
*Attorney, Agent, or Firm*—Robert A. Green

[57] ABSTRACT

The disclosure is of an air ion and charge detector comprising a liquid crystal display device having an indicator electrode and a reference electrode, and connected to detect air ions or electrical charge and provide a visual indication thereof.

8 Claims, 8 Drawing Figures

AIR ION AND CHARGE DETECTOR

BACKGROUND OF THE INVENTION

Known air ion indicators or meters employ some kind of electronic amplification circuitry in order to operate a light or meter from the minute charges obtainable from air ions. An amplifier requires additional power sources such as a power supply or a battery. Electrostatic charge meters which sometimes are used as air ion indicators employ two batteries in order to indicate positive or negative charges.

The above-mentioned requirements make portable air ion indicators or meters relatively complicated, and relatively expensive to manufacture and to operate.

DESCRIPTION OF THE PREFERRED EMBODIMENTS

Figure 1:
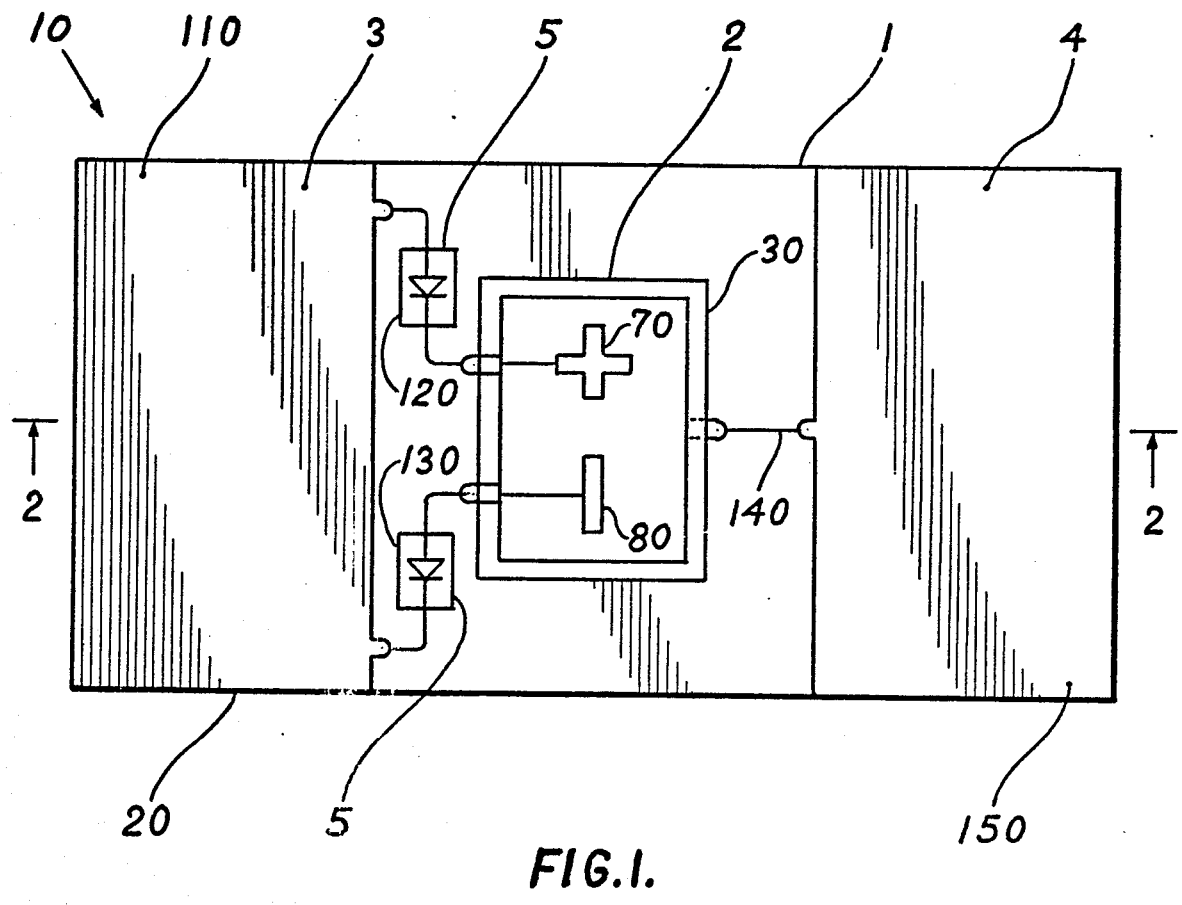
FIG. 1 is a plan view of the invention.
Figure 2:
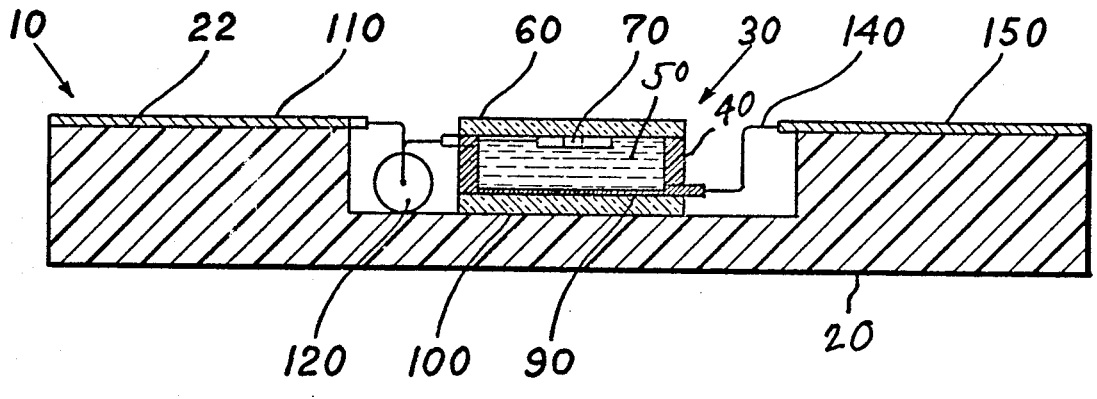
FIG. 2 is a sectional view along the lines 2—2 in FIG. 1.

The air ion indicator of the invention 10, in one embodiment, includes a relatively rigid support plate 20 having a top surface 22 with a liquid crystal display device 30 mounted in a depression on the central portion of the top surface thereof. The liquid crystal display device 30 includes an envelope 40 which is filled with a liquid crystal medium 50 and includes a glass face plate 60, on the inner surface of which are mounted two transparent indicator electrodes 70 and 80, of NESA or the like, one in the form of a plus sign and one in the form of a minus sign. A common reference electrode 90 is provided within the envelope on the base 100 of the envelope and opposite the electrodes 70 and 80. The electrodes have suitable portions for making connections to external circuit elements.

A relatively large-area metal ion collector plate 110 is provided on the top surface 22 of the insulating plate 20 adjacent to one end thereof and is connected through one diode 120, oriented as shown, to the plus sign electrode 70. The collector plate 110 is also connected through a second diode 130, oriented oppositely to diode 120, to the minus sign electrode 80. The reference electrode 90 is connected by lead 140 to a second large-area plate 150 secured to the top surface 22 of the insulating plate at the end opposite the first large-area plate 110.

In operation of the invention, the operator grasps the plate 150 with his fingers to provide a ground connection, and, if ions are present in the air, they will land on the plate 110. As soon as the ions touch the plate 110, they lose their charge and become uncharged atoms or molecules. The plate 110 thus acquires a charge, and its voltage rises and an electric current thus flows through one of the diodes 120 or 130, which discriminate between the positive and negative charges acquired by the collector plate from the air ions, and provides current flow to the proper display or indicator electrode 70 or 80 to provide a visual display thereof. The liquid crystal device will act as a charged capacitor and hold the opposite charges on its plates.

It is noted that the present invention, including the large-area collecting plate 110 and liquid crystal display device, requires no power source.

It is noted that the device 10 may also be used to detect electrical charge in the air around it. Thus, it may be used to detect emanations from a radio antenna or automobile ignition, and it will detect static charge on a surface. For such use, the device would need only one electrode 70 or 80 which would be provided as a disk or in any other suitable shape.

Figure 3:
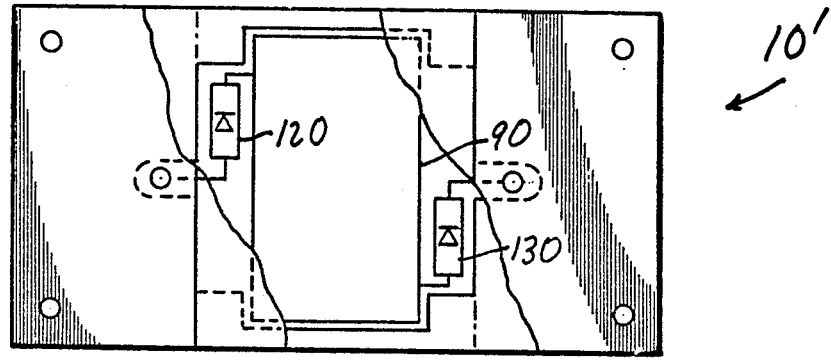
FIG. 3 is a bottom view, partly cut away, of a modification of the invention.
Figure 4:
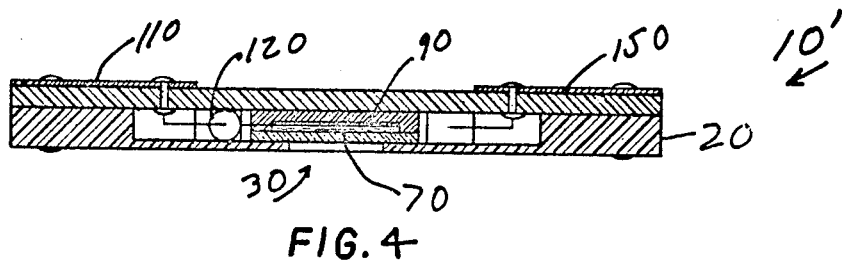
FIG. 4 is a sectional view of the device of FIG. 3.
Figure 5:
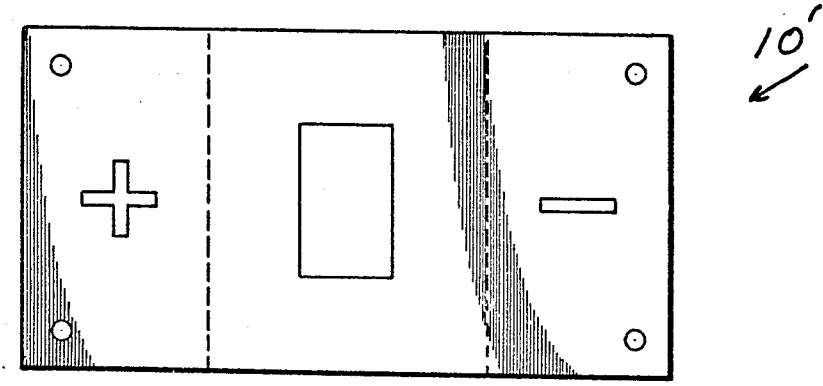
FIG. 5 is a plan view of the device of FIG. 3.

The device 10 may be modified as device 10' shown in FIGS. 3, 4, and 5, wherein parts which are the same as in device 10 carry the same reference numerals. In device 10', electrode 70 may take any shape since a character display is not required. Electrode 70 is connected through a diode 120, oriented as shown, to plate 110, and electrode 80 is connected through oppositely oriented diode 160 to plate 150. One plate may carry a plus sign, and the other may carry a minus sign, as shown in FIG. 5.

The device 10' is used by having the fingers grasp the plates 110 and 150, one after the other, in order to get an indication. The polarity of ions in the air will be shown by the sign of the ungrounded plate. It is noted that the device 10' may also be used to detect a static charge on a surface by sensing the electric field which surrounds the charged surface. For such use, the device is held by one of the plates 110 or 150 and moved toward the charged surface. If there is a charge on the surface, there will be an indication and the charge polarity will be shown by the sign of the ungrounded plate. The opposite charge will be indicated by moving the device away from the charged surface.

The device 10' could be used also to indicate the presence of alternating current fields. For this purpose, both plates 110 and 150 are held by the hand. The alternating current field will be sensed by the reference electrode 90 of the liquid crystal display, and, in combination with the two diodes 120 and 130, will indicate the presence of the alternating electric field.

Figure 6:
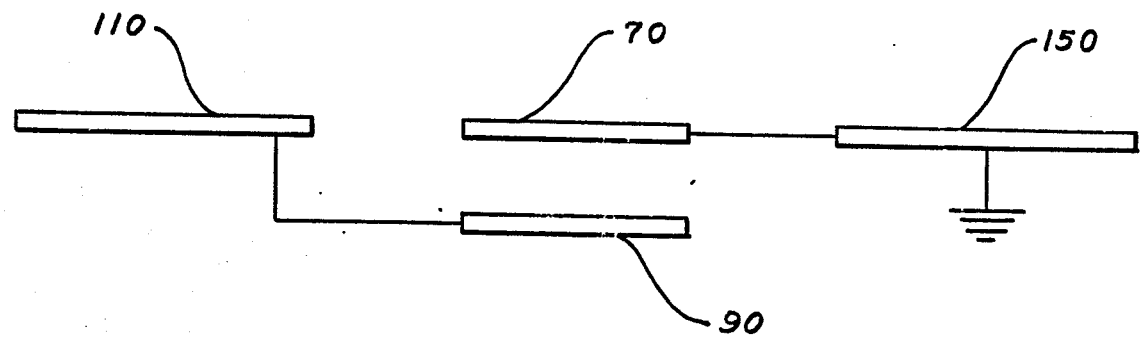
FIG. 6 is a schematic representation of the invention illustrating one mode of operation.
Figure 7:
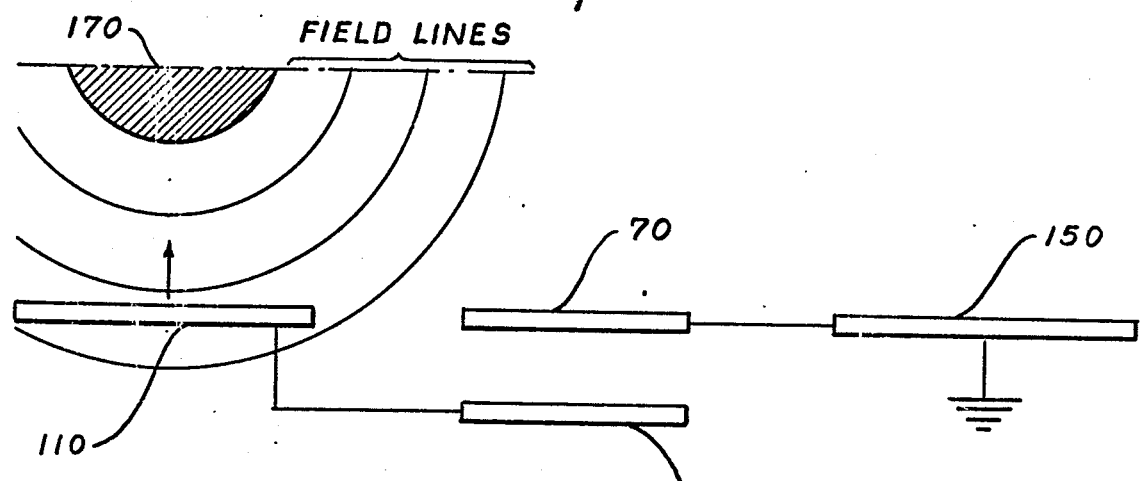
FIG. 7 is a schematic representation of the invention illustrating another mode of operation.
Figure 8:
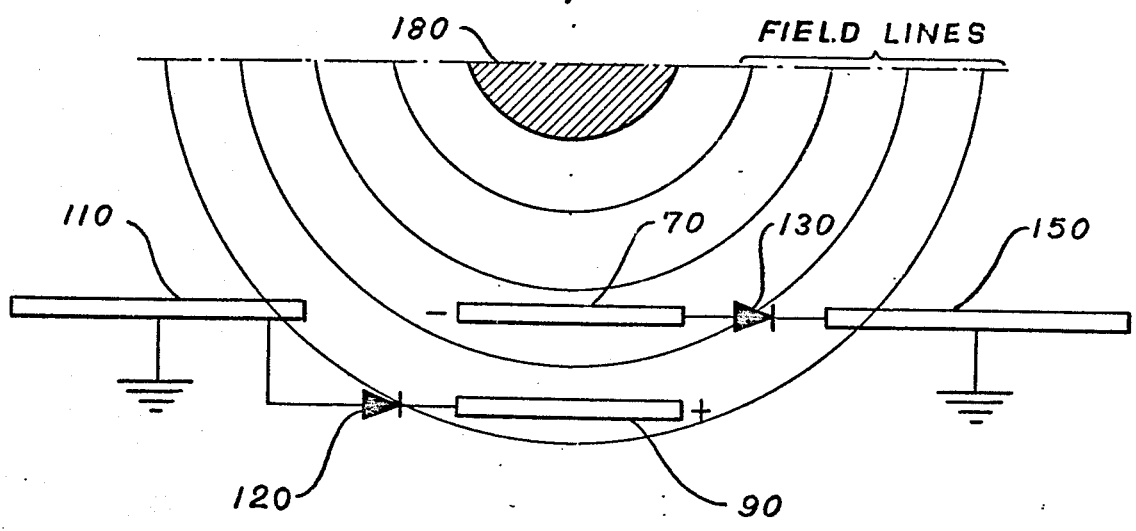
FIG. 8 is a schematic representation of the invention illustrating still another mode of operation.

The various modes of operation of the invention are illustrated with respect to FIGS. 6, 7 and 8, in which the invention is shown schematically. In FIG. 6, diodes are omitted, and, in operation of the apparatus to detect air ions, plate 150 is held by the fingers and is thus grounded, and plate 110 is exposed to the air. If ions, say positive ions, are present, they will land on plate 110 and charge the plate positively. Electrode 90 will become positive, and electrode 70 will become negative, and a visual indication will be provided in the LCD as a result of the charges on its electrodes.

The arrangement of FIG. 7 can be used to detect an electric field adjacent to a charged surface 170. In this case, the device is held by plate 150, and it is moved through the electric field surrounding the wire, and plate 110 becomes charged as it cuts the electric field lines, and the LCD provides a visual indication as above.

The device 10 having diodes 120 and 130 can be used to detect an electric field produced by the A. C. current in wire 180 (FIG. 8). In this case, both plates 110 and 150 are grounded. The A. C. field produces alternating charges on both electroconductive surfaces 70 and 90 of the LCD. The voltage difference between the plates 70 and 90 is produced by the diodes 120 and 130 which provide unidirectional current flow.

What is claimed is:

1. An air ion and electric field detector comprising two electroconductive surfaces insulated from each other, a liquid crystal display having a large-area reference electrode and two small-area indicating electrodes, one in the shape of a plus sign and one in the shape of a minus sign, the reference electrode connected to one of the conductive surfaces, the two indicating electrodes connected to the other surface through two diodes, one oriented to pass the current to the plus sign, the other from the minus sign to the conductive surface.

2. An air ion and electric field detector comprising two exposed electroconductive surfaces insulated from each other, a liquid crystal display device having a large-area reference electrode and a small-area indicating electrode, each connected to one of said electroconductive surfaces, and two diodes, one connected to one of the electroconductive surfaces and the other connected to one of the liquid crystal electrodes, the diodes being oriented to pass current from one electroconductive surface through the liquid crystal display to another.

3. The air ion and electric field detector of claim 2 including a housing, made of insulating material, containing the liquid crystal display and the diodes and a printed circuit board cover having exposed electroconductive surfaces, the housing having an opening to expose the liquid crystal display and plus and minus signs located behind the electroconductive surfaces.

4. An air ion and electric field detector comprising first and second electroconductive surfaces insulated from each other and exposed to the atmosphere, a liquid crystal display device having a first electrode and a second electrode associated with a liquid crystal medium, a first diode connected between said first surface and said first electrode and a second diode connected between said second surface and said second electrode, said diodes being oriented so that, when one of said surfaces becomes electrically charged with respect to the other, current flows in said display device and said first and second electrodes provide a visual indication of such current flow.

5. The apparatus defined in claim 4 wherein at least one of said electrodes is in the form of a character.

6. The apparatus defined in claim 4 wherein said first and second electrodes are small-area electrodes, one having the shape of a plus sign and the other having the shape of a minus sign.

7. An air ion and electric field detector comprising two electroconductive surfaces insulated from each other, and a liquid crystal display having a reference electrode and at least one indicating electrode in the shape of a character, the reference electrode being coupled through a first diode to one of the conductive surfaces, and the character electrode being coupled through a second diode to the other surface, said second diode being oriented to pass current to the character electrode, the first diode being oriented to pass current from the character electrode to the other conductive surface.

8. An air ion and electric field detector comprising a housing, a liquid crystal display device in said housing including first and second internal electrodes in operative relation with a liquid crystal medium therein, first and second external electrodes spaced apart on said housing and accessible to the user of the detector whereby the user can grasp said first external electrode to, in effect, ground the first external electrode electrically, and means electrically connecting said first external electrode to said first internal electrode and said second external electrode to said second internal electrode whereby, when said first external electrode is grounded and said external electrode becomes electrically charged due to receiving electrical charges from the atmosphere, said internal electrodes provide a visual indication of the receipt of such electrical charges.

* * * * *